United States Patent [19]

Takehisa

[11] 4,440,167
[45] Apr. 3, 1984

[54] ANESTHETIZER FOR DENTAL TREATMENT

[75] Inventor: Shigeru Takehisa, Tokyo, Japan

[73] Assignee: Kabushikikaisha Yoshida, Tokyo, Japan

[21] Appl. No.: 327,472

[22] Filed: Dec. 4, 1981

[30] Foreign Application Priority Data

Dec. 26, 1980 [JP] Japan .................. 55-186503[U]

[51] Int. Cl.³ .............................................. A61B 17/36
[52] U.S. Cl. .............................. 128/303.1; 128/399; 433/32; 62/3; 62/293
[58] Field of Search ................ 128/303.1, 399–403, 128/742, 741; 62/293, 3, 259.3; 604/20, 21; 433/31

[56] References Cited

U.S. PATENT DOCUMENTS

| | | | |
|---|---|---|---|
| 2,387,258 | 10/1945 | Hague | 128/303.1 |
| 3,133,539 | 5/1964 | Eidus | 128/303.1 |
| 3,369,549 | 2/1968 | Armao | 128/303.1 |
| 3,421,508 | 1/1969 | Nestrock | 128/303.1 |
| 3,467,104 | 9/1969 | Burbridge et al. | 128/400 |
| 3,674,031 | 7/1972 | Weicke | 128/303.1 |
| 4,308,013 | 12/1981 | Major | 128/742 |

Primary Examiner—Edward M. Coven
Assistant Examiner—Max F. Hindenburg
Attorney, Agent, or Firm—Birch, Stewart, Kolasch & Birch

[57] ABSTRACT

An anesthetizer for dental treatment adapted to anesthetize the defective part of a tooth or gums by freezing. The anesthetizer comprises a hollow tubular anesthetizer body which is branched into a pair of branch tubes having ends opposing to each other with a suitable gap therebetween. A cap is detachably fitted around the end of each branch tube. The top of each cap is closed by a plate-type thermoelectric element with a colder surface directly outwardly. A connecting terminal is projected from the base end of each cap. Conductors for electrically energizing the thermoelectric element and conduits for supplying and discharging a fluid are extended through and sealed in the hollow anesthetizer body. In use, the cold side of the thermo-electric element is placed in contact with the outer surface of the defective part of the tooth or gums to freeze the same to a large depth to realize the anesthetized state without using any anesthetic agent.

4 Claims, 3 Drawing Figures

ANESTHETIZER FOR DENTAL TREATMENT

BACKGROUND OF THE INVENTION

The present invention relates to an anesthetizer used for dental treatment under local anesthetic and, more particularly, to an anesthetizer adapted to effect a freeze-anesthetic making use of the cooling power of thermoelectric elements.

Hitherto, in order to extract a tooth or cut the gums, the gums are anesthetized to a deep part thereof by means of a hypodermic needle. There has been no better method for relieving the patient from the pain during penetration by the hypodermic needle than merely to apply the gum surface with an anesthetic in advance to the driving of the hypordemic needle. Such a method cannot relieve the patient from the pain satisfactorily.

SUMMARY OF THE INVENTION

Accordingly, an object of the invention is to provide an anesthetizer for dental treatment capable of effecting an instantaneous freeze-anesthetic rapidly to a large depth of the gums locally, by merely contacting with the gums. The anesthetizer of the invention has a small overall dimensions and is shaped for an easier handling in the limited space of the oral cavity. The cooling or freezing device provided at the end of the anesthetizer has an extremely small size thanks to the use of a thermoelectric element.

Namely, according to the invention, there is provided an anesthetizer for dental treatment comprising: a hollow tubular anesthetizer body consisting of a tube branched into a pair of branch tubes having ends opposing to each other with a suitable gap therebetween; caps detachably fitted around the opposing ends of the branch tubes; plate type thermoelectric elements secured to free ends of the caps so as to form the top surfaces of respective caps, each thermoelectric element having a colder surface directed outwardly; connecting terminals projected from the base ends of respective caps; and conductors and fluid conduits for cooling the hotter surfaces of the thermoelectric elements, the conductors and the fluid conduits being extended through and sealed in the hollow tubular anesthetizer body via the tube.

As is well known, the thermoelectric elements are the elements which can generate or absorb heat due to Peltier effect. Especially, a thermoelectric element consisting of a combination of P-type and N-type semiconductor compounds, such as bismuth telluride, has a large calorific power or endothermic power to provide a large temperature difference. This type of elements, therefore, has been broadly used as heating devices in various industrial equipments, medical instruments and so forth.

According to the invention, it is possible to obtain a sufficiently high anesthetizing effect by utilizing, as the cooling mechanism, a square tabular panel of commercially available thermoelectric element, having an extremely small size such as 4 to 10 mm in side length and 2 to 4 mm or greater in thickness. This panel is designed and constructed to provide a temperature difference of 50° C. As is well known, one of the surfaces having the higher temperature, i.e. the hotter surface, exhibits a temperature which is the sum of the temperature of the colder side and the temperature produced by the heat generated by the electric current applied thereto. Therefore, assuming here that the hotter side of the panel is maintained at 50° C. through the heat radiator, the colder side of the panel exhibits a temperature of 0° C. provided that an electric current of 16 A is supplied at a voltage of 3.1 V. Similarly, when an electric current of 20 A is applied at a voltage of 3.75 V, the colder side of the panel exhibits a temperature of −6° C. provided that the hotter side is maintained at 50° C. If the hotter side of the panel is forcibly cooled down to a temperature below 32° C., the colder side of the panel is cooled to constitute a cooling surface of −10° C. It is still possible to provide a cooling surface of −40° C. by further cooling the hotter side forcibly.

The invention will be fully understood from the following description of the preferred embodiment taken in conjunction with the accompanying drawings.

DESCRIPTION OF THE PREFERRED EMBODIMENT

Figure 1:
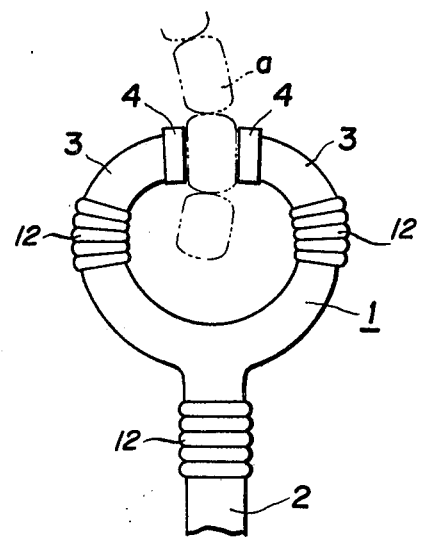
FIG. 1 is a front elevational view of an anesthetizer in accordance with the invention.
Figure 2A:
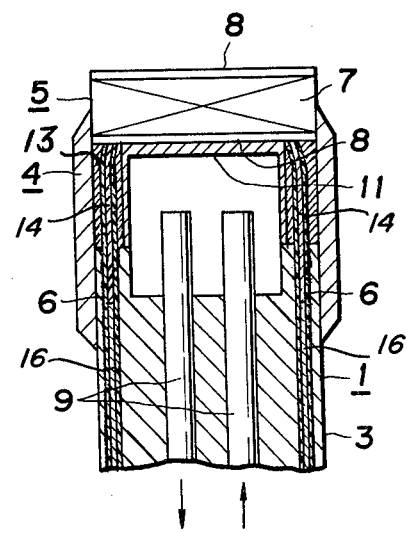
FIG. 2A is a vertical sectional view of an essential part of the anesthetizer shown in FIG. 1.
Figure 2B:
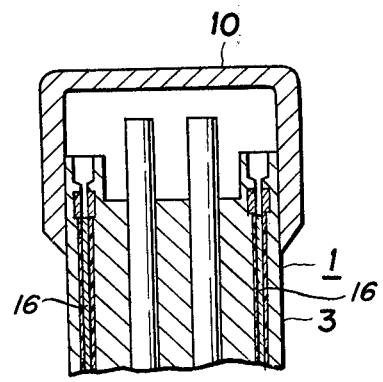
FIG. 2B is a vertical sectional view similar to that shown in FIG. 2A with a cap removed therefrom and a plug fitted thereto insteadly of the cap.

Referring to the drawings, the anesthetizer embodying the present invention has a hollow tubular anesthetizer body 1 or support means consisting of a lower half part constituted by a tube 2 and an upper half part constituted by a pair of branch tubes 3,3 branching from the tube 2. The tube 2 and the branch tubes 3, 3 may consist of an integral body. However, the tube 2 and the branch tubes 3, 3 might be separately manufactured. Flexible portions 12 are interposed in the tube 2 and the branch tubes 3, 3 as seen in FIG. 1 so as to facilitate the use of the anesthetizer of the present invention in the limited space of an individual's mouth due to its flexibility. Caps 4,4 are detachably secured to the ends of the branch tubes 3,3. As will be clearly seen from FIG. 2A, a thermoelectric element 5 is secured to the top end of the cap 4 with its colder surface directed outwardly. A hollow support member 13 is disposed in the cap or the hollow body member 4, an end portion of the hollow support member 13 being attached to a hotter surface of the thermoelectric element 5. A pair of power lines 14, 14 from the thermoelectric element 5 are provided in the hollow support member 13. End portions of the power lines 14, 14 being connected to a pair of connecting terminals 6, 6 which are provided at the end portions of branch tubes 3, 3. The connecting terminals 6, 6 are connected with a power source through lines 16, 16 so as to activate the thermoelectric element 5. The thermoelectric element 5 consists of a panel 7 of the aforementioned semiconductor compound, and ceramic plates 8,8 between which the panel 7 is sandwiched.

A pair of fluid conduits 9,9 having opened upper ends are projected from the end portion of each branch tube 3 of the anesthetizer body 1. A blower connected to the lower end of the tube 2 supplies one of the fluid conduits 9 with cooling air. The cooling air is introduced into the cavity within the cap 4 and effectively cools the lower ceramic plate 8, and is discharged from the cavity through the other fluid conduit 9. The use of air as the cooling medium is not essential. Namely, it is possible to use water in place of cooling air. In such a case, needless to say, it is necessary to provide a watertight joint at junctures between, for example, the branch tube 3 and the associated cap 4. For the convenience's sake, it is adviceable to form suitable portions of the branch tubes 3,3 and the tube 2 with a flexible and elastic material so that the branch tubes 3,3 and the tube 2 may be flexed as desired.

In order to enhance the cooling effect, it is preferred to attach a heat sink 11 to the hotter side of the panel 7.

It is also preferred to attach a thermistor (not shown) to colder side of the thermoelectric element 7. By connecting such a thermistor to an external thermometer, photo-emitting diode, buzzer or the like device, it is possible to detect the temperature change of the colder side quite easily. It is also possible to maintain a substantially constant temperature of the colder side of the thermoelectric element, by connecting the thermistor to a bimetal.

For effecting the anesthetic, the dentist grips a portion of the tube 2 and brings the caps 4,4 into contact with the defective part of the gums from both sides of the latter. In consequence, the defective part is instantaneously frozen to a large depth. If the occasion demands the freezing of the gums only from one side, the cap 4 of one of the branch tubes is detached and a plug 10 is fitted insteadly.

In order to prevent any accidental freezing of other portions of the mouth than the defective gums, e.g. lips, tongue and so forth, when the anesthetizer is inserted, it is preferred to coat beforehand the surfaces other than those of the caps 4,4 with a suitable heat insulating material. It is also possible to reduce the pain due to rapid cooling, by increasing the source voltage gradually by means of a variable resistor or the like. In the event that the anesthetizer is hardly separable from the gums or teeth due to the complete freezing, it is possible to raise the temperature of the anesthetizer for easy separation simply by changing the polarity of the source.

As will be understood from the foregoing description, the anesthetizer of the invention can suitably be used for various dental treatments such as extraction of a tooth, opening of gums by cutting, removal of bone, cutting and shaping of teeth, removal of dental pulp and so forth, because the anesthetizer of the invention can be handled quite easily even in the limited space of the oral cavity, thanks to the sufficiently reduced size. In addition, the simplified construction eliminates fear of breakdown almost completely.

It is also advantageous that the anesthetizer of the invention causes no substantial unfavourable side effect, unlike the conventional apparatus using an anesthetic. The anesthetizer of the invention offers also an advantage that the judgement as to whether the teeth nerve has been dead or alive, when the tooth has been coated by a metal, by observing the reaction to application of cold and heat from the outside of the tooth.

Furthermore, the dental treatment can be finished in a shorter period of time as compared with conventional technic, thanks to a rapid recovery from the anesthetized state.

What is claimed is:
1. An anesthetizer for dental treatment comprising:
   a hollow tubular anesthetizer body consisting of a tube branched into a pair of branch tubes having ends opposing to each other;
   a gap of a predetermined distance being positioned therebetween for placing said pair of branch tubes on each side of a single tooth, gum area;
   caps detachably fitted on opposing ends of the branch tubes;
   plate-type thermoelectric elements secured to free ends of the caps so as to form the top surfaces of respective caps, each thermoelectric element having a colder surface directed outwardly toward said gap with a warmer surface being confined with said caps;
   connecting terminals projected from the branch tubes and being operatively connected to each of said thermoelectric elements; and
   fluid conduits for cooling the hotter surfaces of the thermoelectric elements, said fluid conduits extending through said hollow tubular anthetizer body via the branch tubes.
2. An anesthetizer according to claim 1, and further including a heat sink member operatively positioned adjacent to a hotter surface of said thermoelectric element, said heat sink member being secured to said caps.
3. An anesthetizer according to claim 1, wherein said fluid conduits are connected to an air blower for cooling a hotter portion of said thermoelectric element.
4. An anesthetizer according to claim 1, wherein said fluid conduits are connected to a water supply for cooling a hotter portion of said thermoelectric element.

* * * * *